United States Patent
Vora et al.

(10) Patent No.: US 10,537,403 B2
(45) Date of Patent: Jan. 21, 2020

(54) PASSIVE RFID BASED HEALTH DATA MONITOR

(71) Applicant: Drexel University, Philadelphia, PA (US)

(72) Inventors: Shrenik Vora, Philadelphia, PA (US); Timothy Kurzweg, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 657 days.

(21) Appl. No.: 15/162,544

(22) Filed: May 23, 2016

(65) Prior Publication Data

US 2016/0338798 A1    Nov. 24, 2016

Related U.S. Application Data

(60) Provisional application No. 62/165,165, filed on May 21, 2015.

(51) Int. Cl.
| | |
|---|---|
| *A61B 90/98* | (2016.01) |
| *A61B 5/00* | (2006.01) |
| *A61B 5/0456* | (2006.01) |
| *A61B 5/08* | (2006.01) |
| *A61B 5/0245* | (2006.01) |

(52) U.S. Cl.
CPC ............ *A61B 90/98* (2016.02); *A61B 5/0006* (2013.01); *A61B 5/0245* (2013.01); *A61B 5/0456* (2013.01); *A61B 5/0816* (2013.01); *A61B 2503/04* (2013.01); *A61B 2560/0219* (2013.01)

(58) Field of Classification Search
None
See application file for complete search history.

(56) References Cited

U.S. PATENT DOCUMENTS

| | | |
|---|---|---|
| 7,595,723 B2 | 9/2009 | Heitzmann et al. |
| 7,827,011 B2 | 11/2010 | DeVaul et al. |
| 7,979,111 B2 | 7/2011 | Acquista |
| 8,115,600 B2 | 2/2012 | Stevenson et al. |
| 8,361,000 B2 | 1/2013 | Gaspard |
| 8,454,528 B2 | 6/2013 | Yuen et al. |
| 8,527,038 B2 | 9/2013 | Moon et al. |
| 8,564,452 B2 | 10/2013 | Schaible et al. |
| 8,750,971 B2 | 6/2014 | Tran |

(Continued)

FOREIGN PATENT DOCUMENTS

| | | |
|---|---|---|
| CN | 202408883 U | 9/2012 |
| WO | 2014100687 A2 | 6/2014 |

OTHER PUBLICATIONS

Ajitha et al.—Improving RFID Tag Efficiency by QAM Backscatter Modulation; 2013 IEEE International Conference on RFID (Year: 2013).*

(Continued)

*Primary Examiner* — David J. McCrosky
*Assistant Examiner* — Jay B Shah
(74) *Attorney, Agent, or Firm* — Schott, P.C.

(57) ABSTRACT

A wearable, wireless and battery-free continuous health monitor includes an RFID tag used as an On-Off Keying Device to measure the heart rate. The tag's returned signal strength variations are used to calculate the respiration rate. Machine learning algorithms are employed to determine the health parameters.

7 Claims, 12 Drawing Sheets

(56) References Cited

U.S. PATENT DOCUMENTS

| | | | |
|---|---|---|---|
| 8,920,332 | B2 | 12/2014 | Hong et al. |
| 8,945,017 | B2 | 2/2015 | Venkatraman et al. |
| 8,977,351 | B2 | 3/2015 | Kivistö |
| 9,282,893 | B2 | 3/2016 | Longinotti-Buitoni et al. |
| 9,323,966 | B2 | 4/2016 | Deyle |
| 2007/0232867 | A1 | 10/2007 | Hansmann |
| 2011/0263950 | A1 | 10/2011 | Larson et al. |
| 2013/0060098 | A1 | 3/2013 | Thomsen et al. |
| 2013/0278076 | A1* | 10/2013 | Proud .................. G06F 8/65 307/104 |
| 2014/0094675 | A1 | 4/2014 | Luna et al. |
| 2014/0100432 | A1 | 4/2014 | Golda et al. |
| 2014/0135593 | A1 | 5/2014 | Jayalth et al. |
| 2014/0316229 | A1 | 10/2014 | Tognetti et al. |
| 2015/0099941 | A1 | 4/2015 | Tran |
| 2015/0129664 | A1 | 5/2015 | Brar |
| 2016/0034731 | A1 | 2/2016 | Lin |
| 2016/0051153 | A1 | 2/2016 | Mously |
| 2016/0120434 | A1 | 5/2016 | Park et al. |

OTHER PUBLICATIONS

Besnoff et al.—Battery-Free Multichannel Digital ECG Biotelemetry using UHF RFID Techniques; International Journal of Scientific & Engineering Research, vol. 4, Issue 4, Apr. 2013 (Year: 2013).*
Vora et al.—Passive RFID Tag based Heart Rate Monitoring from an ECG Signal 2015 37th Annual International Conference of the IEEE (Year: 2015).*
Vora et al.—Unconventional Biosignal Sensing with Passive RFID Tags, The Bridge; 2016 (Year: 2016).*
Dementyev et al—A Wearable UHF RFID-Based EEG System—2013 IEEE International Conference on RFID (Year: 2013).*
Hannan et al.—Modulation Techniques for Biomedical Implanted Devices and Their Challenges Sensors 2012, 12, 297-319 (Year: 2012).*
Artem Dementyev, Joshua R. Smith, "A Wearable UHF RFID-Based EEG System," University of Washington, 2013 IEEE, Seattle, WA, Entire Document.
B.-J. Jang, S.-H. Wi and J.-G. Yook, M.-Q. Lee, K.-J. Lee, "Wireless Bio-Radar Sensor for Heartbeat and Respiration Detection," Progress in Electromagnetics Research C, vol. 5, 149-168, 2008.
Christoph Brüser, Kurt Stadlthanner, Andreas Brauers, Steffen Leonhardt, "Applying Machine Learning to Detect Individual Heart Beats inBallistocardiograms," IEEE EMBS, Buenos Aires, Argentina, 2010, Entire Document.
Damiano Patron, Timothy Kurzweg, Adam Fontecchio, Genevieve Dion, and Kapil R. Dandekar, "Wireless Strain Sensor Through a Flexible Tag Antenna Employing Inductively-Coupled RFID Microchip," Drexel University, Philadelphia, PA, IEEE, 2014, Entire Document.
David M W Powers, "Evaluation: From Precision, Recall and F-Factor to ROC, Informedness, Markedness & Correlation," Flinders University of South Australia School of Informatics and Engineering, South Australia, Dec. 2007, Entire Document.
I-Jan Wang, Lun-De Liao, Yu-Te Wang, Chi-Yu Chen, Bor-Shyh Lin, Shao-Wei Lu, Chin-Teng Lin, "A Wearable Mobile Electrocardiogram Measurement Device with Novel Dry Polymerbased Electrodes," Tencon 2010, IEEE, Entire Document.
Jordan S. Besnoff, Travis Deyle, Reid R. Harrisony, Matthew S. Reynolds, "Battery-Free Multichannel Digital ECG Biotelemetry using UHF RFID Techniques," Duke University, IEEE, 2013, Durham, NC, Entire Document.
Kong Y. Chen, Kathleen F. Janz, Weimo Zhu, and Robert J. Brychta, "Re-Defining the Roles of Sensors in Objective Physical Activity Monitoring," National Institute of Health, 2012, Entire Document.
M. Caldaraa, B. Nodaria, V. Rea, B. Bonandrinib, "Miniaturized and low-power blood pressure telemetry system with RFID interface," Procedia Engineering, ScienceDirect, vol. 87, 2014, pp. 344-347, Italy.
Matthai Philipose, Joshua R. Smith, Bing Jiang, Alexander Mamishev, Sumit Roy, Kishore Sundara-Rajan, "Battery-Free Wireless Identification and Sensing," Energy Harvesting & Conservation, IEEE, 2005, Entire Document.
Ping Jack Soh, Guy A.E. Vandenbosch, Marco Mercuri, and Dominique M.M.-P. Schreurs, "Wearable Wireless Health Monitoring," IEEE, May 2015, Entire Document.
Robert Matthews, Neil J. McDonald, Paul Hervieux, Peter J. Turner, and Martin A. Steindorf, "A Wearable Physiological Sensor Suite for Unobtrusive Monitoring of Physiological and Cognitive State," IEEE, France, 2007, Entire Document.
Samira Jaafari, "Adaptive Filtering for Heart Rate Signals," San Jose Statue University, SJSU ScholarWorks, May 2014, Entire Document.
Stanislaw Osowski, Linh Tran Hoai, and Tomasz Markiewicz, "Support Vector Machine-Based Expert System for Reliable Heartbeat Recognition," IEEE Transactions on Biomedical Engineering, vol. 51, No. 4, Apr. 2004, Entire Document.
W. Mongan, K. Dandekar, G. Dion, T. Kurzweg and A. Fontecchio, "Statistical Analytics of Wearable Passive RFID-based Biomedical Textile Monitors for Real-Time State Classification," Drexel University, IEEE, 2015, Entire Document.
Yu M. Chi and Gert Cauwenberghs, "Wireless Non-contact EEG/ ECG Electrodes for Body Sensor Networks," University of California, San Diego, IEEE 2010, Entire Document.

* cited by examiner

PASSIVE RFID BASED HEALTH DATA MONITOR

CROSS-REFERENCE TO RELATED APPLICATIONS

This application claims the benefit of U.S. Provisional Patent Application Nos. 62/165,165 filed May 21, 2015, and 63/298,544 filed Feb. 23, 2016, which are incorporated herein by reference as if fully set forth herein.

STATEMENT REGARDING FEDERALLY SPONSORED RESEARCH OR DEVELOPMENT

This invention was made with government support under Contract No. 1430212 awarded by the National Science Foundation Partnership for Innovation: Building Innovation Capacity (PFI:BIC) subprogram. The government has certain rights in the invention.

BACKGROUND

A common approach to continuously monitoring a person's health condition, for example heart rate, respiration rate, and the like, requires that the subject wear one or more sensors that are physically coupled to a stationary electrical mains-powered monitoring device. Another common approach is to couple the sensors to a wireless transmitter powered by a portable battery pack. Such approaches can be problematic.

For example, a healthcare provider may be interested in monitoring an infant's heart and respiration rate. However, tethering a baby to lengthy wired devices for continuous monitoring, as is usually done, can be difficult. Besides being uncomfortable, such wired monitors can be hazardous if the baby gets entangled in them. Moreover, monitors that are attached to cumbersome battery packs or mains powered processing units add to the discomfort of the infant.

Over the last decade, there has been a big push towards the development of wearable health monitoring devices. The underlying assumption is that wearable devices will allow for affordable round-the-clock monitoring, which will, in turn, enable early detection and prevention of many diseases. Heart rate monitors and electrocardiogram (ECG) devices are a group of devices that have received wide attention from the wearable devices community. However, research on ECG monitors has been focused on making better wearable sensors and integrating them with a minimal profile. To wirelessly transmit the cardiac information, a battery-powered solution is generally used, together with communication methods like Bluetooth and cellular technologies or prototype radio frequency (RF) transmitters. Batteries add to the size and weight of wearable systems, making them obtrusive and cumbersome.

SUMMARY OF THE EMBODIMENTS

The present invention is a health monitoring system comprising a passively powered, lightweight, unobtrusive wearable sensing device. Illustrative embodiments include a wearable sensing element or electrode coupled to a passive RFID tag, or the RFID tag may be used as a sensor. Also included in illustrative embodiments are a signal amplifier, a wireless power harvester, and a wireless transmitter. The passive RFID tag is used to obtain operating power and to transmit sensed health information. The health information provided by the wearable device may include heart rate information, respiration rate information, and the like. More than one type of wearable device may be worn at a time, or alternatively their monitoring components may be combined into a single wearable device. The wearable device may operate without a battery and without being coupled to a wired power source.

BRIEF DESCRIPTION OF THE DRAWINGS

The accompanying figures are included to provide a further understanding of the invention, and are incorporated in and constitute a part of this specification. The figures illustrate and the detailed description explains various exemplary embodiments and/or aspects, and serve to explain the principles of the invention. The disclosed embodiments are presented as examples, and are not limiting. The scope of the invention is defined by the claims. In the figures:

DETAILED DESCRIPTION OF THE EMBODIMENTS

A health information monitoring system comprises a passive RFID powered wearable component and an RFID reader component. The wearable component may not be tethered to a power source or any other structure, such as a hospital bed, for example. Moreover, the system may be battery-free, eliminating the need for battery replacement and charging.

Passive radio frequency identification (RFID) tagsmay work on power harvested wirelessly, typically from an RFID reader. RFID tags have been used conventionally as a means of identifying objects. For example, they can be used for product identification similar to barcodes, or to track components in a manufacturing setting. For RFID tags to be used in sensor networks, they have to be capable of conveying sensor data along with the tag ID. In its simplest form, an RFID tag can be used as a one-bit transmission device by turning the RFID tag on and off, and having an RFID reader detect the tag's state. For instance, the reader may detect a "1" when the tag is on and a "0" when the tag is off.

Contemporary RFID tags may be capable of storing and transmitting multiple bits of data in addition to a default tag ID. However, writing and storing such data requires additional elements like analog to digital converters (ADCs) and microcontrollers to digitize and store the additional data with the tag ID. Not only would such elements increase the size and complexity of the wearable component, but they would also add to its power requirements. Another drawback of such elements is that they may require significant transmitted data redundancy to achieve an acceptable degree of reliability. For example, one known electroencephalogram (EEG) system requires 92% data overhead and has a range of only about 0.8 meter. The requirement for data overhead adds to the system power consumption. Because power is harvested wirelessly, the higher power demand can significantly degrade the system's range. Accordingly, such additional elements are not used in the disclosed embodiments, but may be used in other embodiments that are not explicitly disclosed.

The disclosed embodiments comprise an unobtrusive, battery-free, wearable component for monitoring health information using one or more passive RFID tags. The health information may include, for example, respiration information obtained from changes in the RFID tag position, heart rate information obtained from an ECG signal, and other information from other types of sensors. The system can be used to wirelessly monitor such aspects of a subject's health information and, in some embodiments, the subject's location when mobile. The system can eliminate the need for the subject to be tethered to a cardiac or other health monitoring system that may be, for example, physically coupled to a hospital bed.

Figure 1:
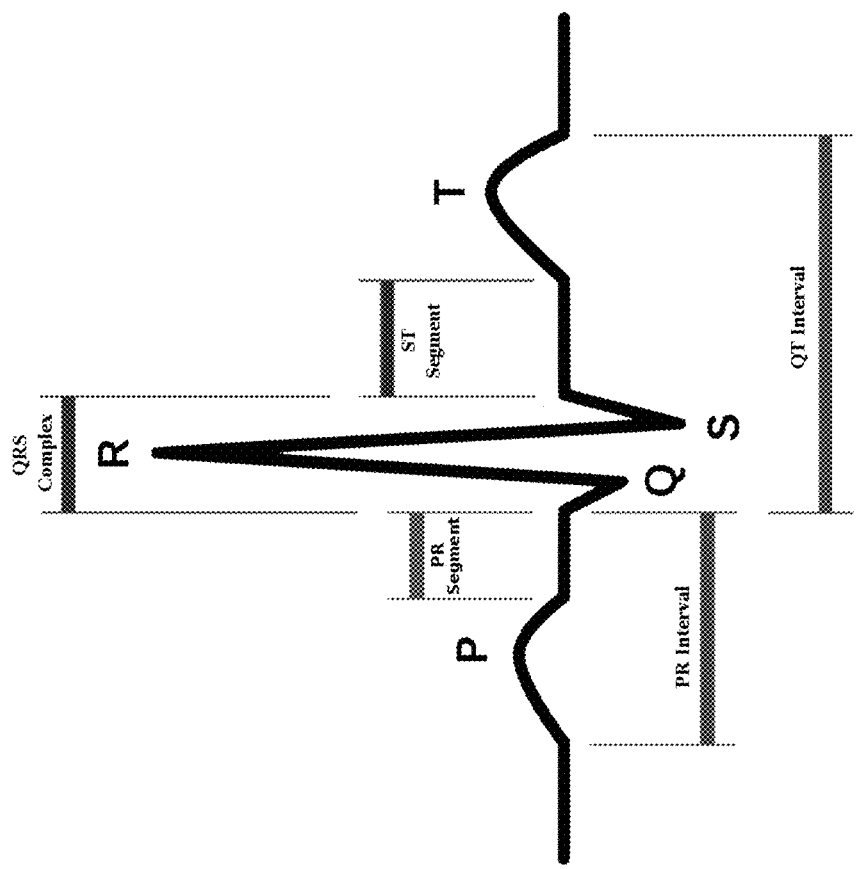
FIG. 1 shows a single cycle of a simplified ECG signal.

FIG. 1 illustrates a single cycle of a typical signal from an electrocardiogram (ECG). The ECG indicates the electrical activity of the heart, typically using electrodes placed on the skin. These electrodes detect the tiny electrical changes on the skin that arise from the heart muscle's electrophysiologic pattern of depolarizing during each heartbeat. During each heartbeat, a healthy heart may have an orderly progression of depolarization that starts with pacemaker cells in the sinoatrial node, spreads out through the atrium, passes through the atrioventricular node down into the fibers spreading down and to the left throughout the ventricles. This orderly pattern of depolarization may give rise to the characteristic ECG tracing. The letters P, Q R, S, and T were long ago arbitrarily assigned to different portions of the ECG waveform, as shown in FIG. 1. The QRS complex represents the rapid depolarization of the right and left ventricles. The ventricles have a large muscle mass compared to the atria, so the QRS complex usually has a much higher peak ("R") than the rest of the waveform. Therefore, the heart rate can be determined by measuring the time between successive R peaks.

To do so, the system may employ on-off keying (OOK) to transmit heart rate. For example, the RFID tag can be turned on by default, and turned off for a predetermined brief duration every time an R peak is detected in the ECG wave. This action of turning the tag off results in a succession of RFID outages corresponding to the ECG peaks. The outages can be detected by the RFID reader and used to determine the heart rate using the equation $$\text{Heart Rate}(BPM) = \frac{60}{T_{R-R}} \quad (1)$$

where "$T_{R-R}$" is the time between successive RFID outages in seconds. This gives the heart rate in beats per minute (BPM).

Figure 2:
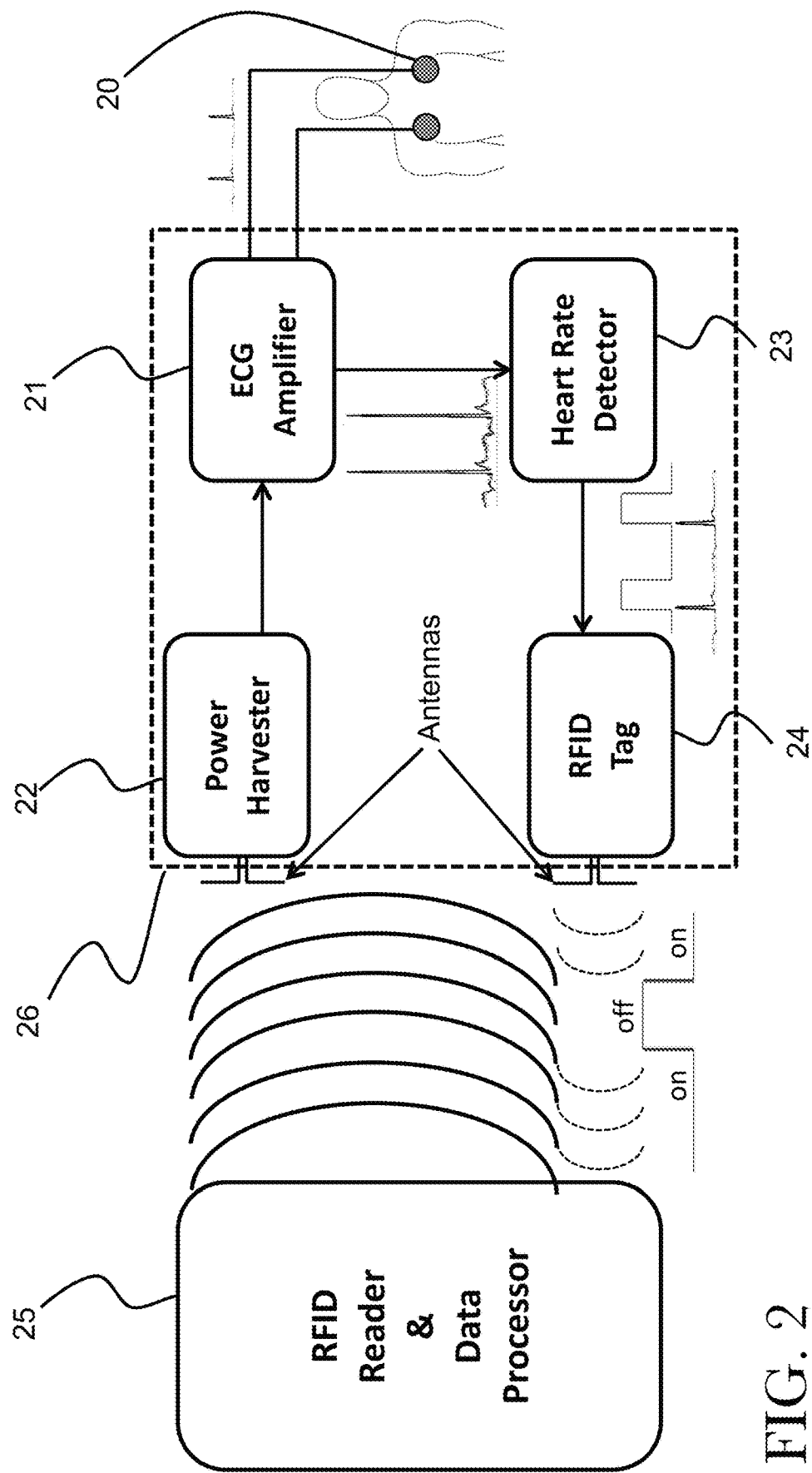
FIG. 2 is a block diagram illustrating an exemplary embodiment of the disclosed system and various signals passing between its elements.

FIG. 2 is a block diagram illustrating components of an exemplary system embodiment. The RFID reader component 25 is at the left of FIG. 2, and the RFID tag component is at the right of FIG. 2, as indicated by the dotted box 26. The RFID tag component comprises certain exemplary elements, and shows the various couplings between them.

The ECG signal is generated using electrodes 20, and input into ECG amplifier 21. The amplitude of the ECG signal input is typically on the order of a couple of millivolts or less (shown by the small waveform to the right of the ECG amplifier) and may amplified in ECG amplifier 21 (shown by the larger waveform below the ECG amplifier). Such amplification requires power, and the power may be obtained using wireless power harvester 22 which obtains energy transmitted by the RFID reader 25. The RFID reader 25 generates a field shown as a series of large concave waves of thick solid lines. In an embodiment, power harvester 22 receives the reader field via an antenna and harvests its energy. In an embodiment, the frequency of the reader field may be matched to the resonant frequency of RFID tag 24. Power harvester 22 outputs DC to passively powered elements including ECG amplifier 21.

The amplifier and any other passively powered elements may be configured to consume as little power as practicable. This is because the passive elements get their power from the power harvester 22. The instantaneous power harvested is proportional to the distance between the power harvester 22 and the RFID reader 25, so the range of the system is directly proportional to the instantaneous power harvested, and the more power the passive elements consume the shorter the effective range of the system. In an embodiment, ECG amplifier 21 may be a simple two lead ECG amplifier circuit similar to those known in the art, but configured to promote full scale output and low power consumption in a small footprint.

The amplified ECG signal is input into heart rate detector 23. In an embodiment, the heart rate detector may comprise a comparator/timer block, and the comparator/timer block may comprise a micropower 555 timer IC that detects the wave peaks R in the ECG signal. The timer's comparator may be configured to determine when the ECG signal exceeds a predetermined threshold such that the R wave is reliably detected. When a wave peak R is detected, the timer may set its output high for a predetermined duration, such as 100 ms. This duration may be user programmable, and may limit the maximum detectable heart rate, for example 500 BPM. After the high output of 100 ms duration, the comparator output is set to low and it is ready to detect the next wave peak R. As shown in the figure to the left of heart rate detector 23, the output of the heart rate detector resembles a binary pulse train with highs of 100 ms duration separated by lows, such that the leading edge of each pulse is separated from the leading edge of the next pulse by a duration that equals the duration between successive R peaks and the corresponding heartbeats.

The output of heart rate detector 23 is input into RFID tag 24. The RFID tag 24 may be arranged to turn on and off based on the signal from the heart rate detector 23. In an exemplary embodiment, the RFID tag 24 may be configured so that its default state is on. For example, with no ECG signal input into the ECG Amplifier, RFID tag 24 remains in its default state and continuously responds to an interrogation signal with its RFID tag ID. When an ECG signal is input into the amplifier, an amplified ECG signal is input into the RFID tag 24. The RFID tag 24 may be configured to turn off when its input (from the output of the heart rate detector 23) goes to its high level, and stays off for the duration of the high level input. The RFID tag 24 may advantageously contain a UHF RFID chip with a direct current input (DCI) that suppresses RF communication from the tag when RFID tag 24 input is set to high. In this embodiment, the tag may be switched on and off without using any additional external circuitry.

The backscatter from RFID tag 24, shown in FIG. 2 as small, concave waves with thin, dashed lines, may be received by the RFID reader 25, which analyzes the waveform received. In an exemplary embodiment, Impinj's Speedway RFID Reader (IPJ-R 1000) may be used with a Laird Technologies 59028PCLJ antenna to read the ultrahigh frequency (UHF) RFID tag. The RFID tag 24 may be advantageously configured to operate with an input voltage between 1.5V and 3V, and a peak current consumption less than 80 µA.

An exemplary system was tested in a test environment (not shown). In the test environment, an ECG simulator was used to generate ECG waveforms at five distinctive heart rates between 30 BPM and 300 BPM. In the test, the RFID reader component and the RFID tag component were spaced approximately three feet from each other. The RFID reader read the tag for a period of three minutes at each heart rate, as is usual, the reader generated an interrogation signal, and the response received from the tag was recorded and time-stamped at regular intervals. These time-stamped data points were then analyzed by the data processor of RFID reader 25 to determine the heart rate, and compared to the known actual heart rate to determine its accuracy. The effective range of the system was also tested by increasing the distance between the RFID reader component and the RFID tag component. In addition, the performance of the system was tested in the presence of an additional dummy RFID tag to study the tested system's ability to operate properly in the presence of a second RFID device.

Figure 3:
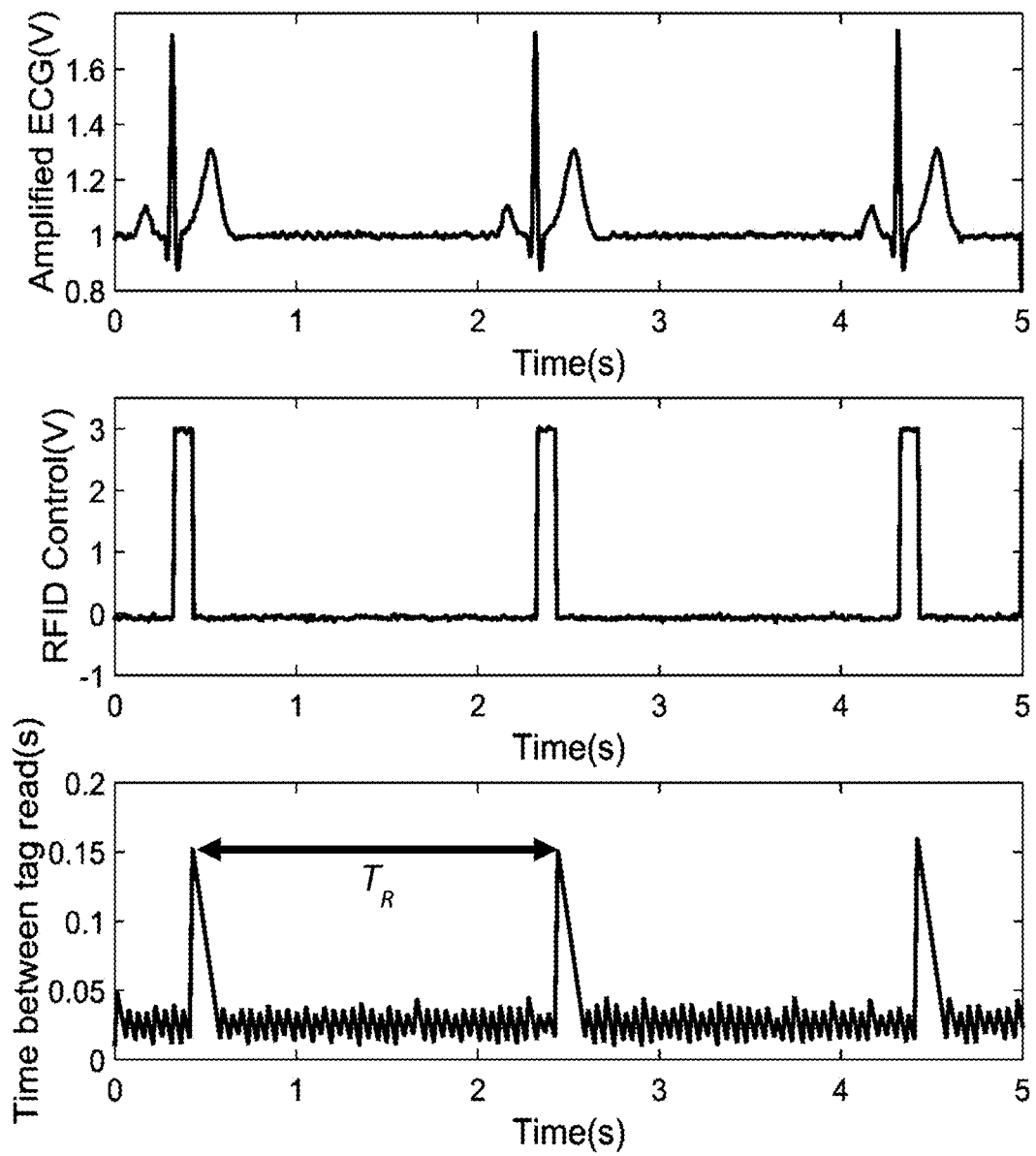
FIG. 3 shows graphs pertaining to heart beat detection for a 30 BPM ECG signal, including an amplified ECG signal (top), timer output to turn RFID tag on/off (middle), and time between successive tag reads (bottom).

An exemplary amplified ECG signal for a 30 BPM wave is shown at the top of FIG. 3. For the 30 BPM signal, the ECG pulse appears every two seconds. The amplified R wave triggers the comparator in the timer causing it to turn the output high for 100 ms. This detection of an ECG pulse is demonstrated in the middle plot of FIG. 3. The system was configured to turn the tag off for 100 ms with every pulse detected, as shown in the middle plot. The time difference between successive tag reads was determined and plotted at the bottom of FIG. 3. It can be clearly seen that there is a spike for every ECG pulse that defines the duration of each pulse *T* R.

Similar results were observed for each of the distinctive exemplary heart rates. Data for all of the exemplary heart rates, which were within the range of 30 BPM and 300 BPM inclusive, is summarized in the following table.

| HR (BPM) | Time (min) | Beats | Average HR (BPM) | Beat-to-beat std dev |
|---|---|---|---|---|
| 30 | 2.99 | 90 | 30.00 | 0.20 |
| 60 | 3.00 | 180 | 59.95 | 0.82 |
| 120 | 3.00 | 360 | 119.99 | 3.67 |
| 180 | 2.99 | 540 | 180.04 | 6.90 |
| 240 | 2.99 | 720 | 240.02 | 15.86 |
| 300 | 2.99 | 899 | 299.92 | 25.65 |

The first column of the table is the beats per minute (BPM) of the ECG waveform used. The second column lists the total duration for each measurement in which detected beats were counted. The third column is the number of heart beats detected by the RFID system within that time. The fourth column is populated by dividing the number of beats in the third column by time in the second column. The beat-to-beat heart rate is determined by measuring the time between successive tag outages and using that in (1) Equation 1, repeated here for convenient reference.

$$\text{Heart Rate}(BPM) = \frac{60}{T_{R-R}}$$

The last column lists the standard deviation of all such beat-to-beat heart rate measurements in the given data set. Heart rates are always presented as an integer, but fractional values are included in the standard deviation calculations in order to better compare accuracy. It can be seen that the average heart rate calculated for all measurements is accurate when sampled for three minutes. But the standard deviation increases as the BPM increases. The standard deviation is lowest for 30 BPM, and highest for 300 BPM. For 30 BPM and 60 BPM, the standard deviation of the beat-to-beat measurement is less than 1, which means that for these heart rates one could simply measure the time difference between successive tag outages and expect to get a very accurate heart beat calculation. However, the standard deviation for the remaining ECG signals is greater than one. It is important to note that the accuracy of the tag timing measurements does not get worse with increasing heart rate. Rather, the same error in time measurement has a larger significance for a higher heart rate, because the time between each heartbeat at the higher rate is shorter than at a lower rate. For example, a 20 ms overestimation in a 30 BPM measurement will cause an error of 2%, while a 20 ms overestimation in a 300 BPM measurement will cause the calculated heart rate to be off by 9%.

The primary source of this error can be explained with reference to the bottom plot in FIG. 3. While the tag is on, the time between successive tag reads may be expected to be constant. However, that was not so in the test case. Instead, the time between successive tag reads varied between about 0.015 s and 0.03 s. Another source of error in the test environment was determined to be that the time taken to turn the tag on/off could vary anywhere within a range of about 2 ms to 20 ms. Moreover, there were instances when tag reads were missed, leading to a longer than expected measured time between successive tag reads. The combination of these factors created variability in the time measured by the system between successive pulses of an ECG pulse rate that was substantially constant. In spite of these variations, the detected heart rates over a longer period were found to be very accurate. As shown in the table above, in the test environment with a 300 BPM signal, the exemplary system detected nearly 900 beats in three minutes. However, the standard deviation of the time between successive detected heart beats was significant. Thus, averaging detected beats of a fast heart rate over a long sample window was found to yield accurate results. However, the three-minute sampling window used in Table I is both impractical and excessive. Accordingly, an analysis of the test data was performed to determine the shortest sampling window within which a reasonably accurate heart rate calculation could be obtained.

Figure 4:
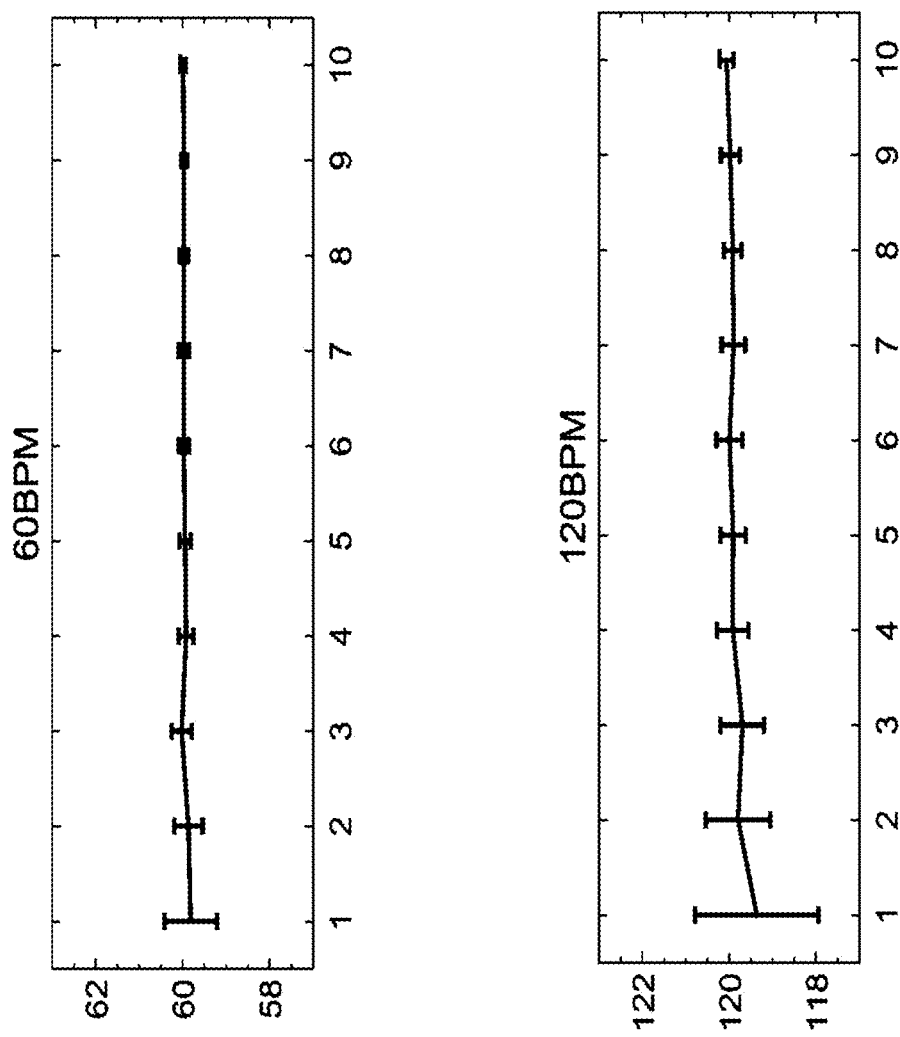
FIG. 4 is a graph of the mean values and standard deviation observed in heart rate calculations over two different sampling windows.

In the analysis, each measurement window was defined to start and end with a detection of a beat. The heart rate within that window is $60*\text{Beats}/T_{sample}$, where "Beats" is the number of heart beats detected in the window, and "$T_{sample}$" is the duration of the sampling window in seconds. FIG. 4 shows plots of the results at 60 BPM and 120 BPM, with sampling windows of 1, 2, . . . 9, and 10 seconds. The average BPM from each sampling window is indicated by the points connected by the substantially horizontal line in each graph. The standard deviation is also shown, represented by the error bars. It can be seen that to obtain a heart rate calculation that is accurate to within 1 BPM, a sampling window of one second was found to be sufficient to obtain a reasonably accurate pulse rate for the 60 BPM signal. However, a sampling window of about 2 seconds was required to obtain the same 1 BPM accuracy for the 120 BPM signal. As noted previously, the higher standard deviation of the faster heart rate can be attributed to the increasing significance of the same error margin in terms of BPM. However, here it is also noted that the standard deviation (error bars) plotted in the bottom graph of FIG. 4 for the 120 BPM ECG signal is lower than the standard deviation shown in column 5 of the table above. This is because the table used a window of three minutes, which is many times larger than the measurement windows from one to 10 seconds plotted in FIG. 4. The longer window produces a far larger number of data points. A greater range of values is observed in the larger window because the greater number of data points from the longer window are much more likely to include some values that arise only infrequently, and even a few outliers. Such values are far less likely to arise in the short windows graphed in FIG. 4.

Figure 5:
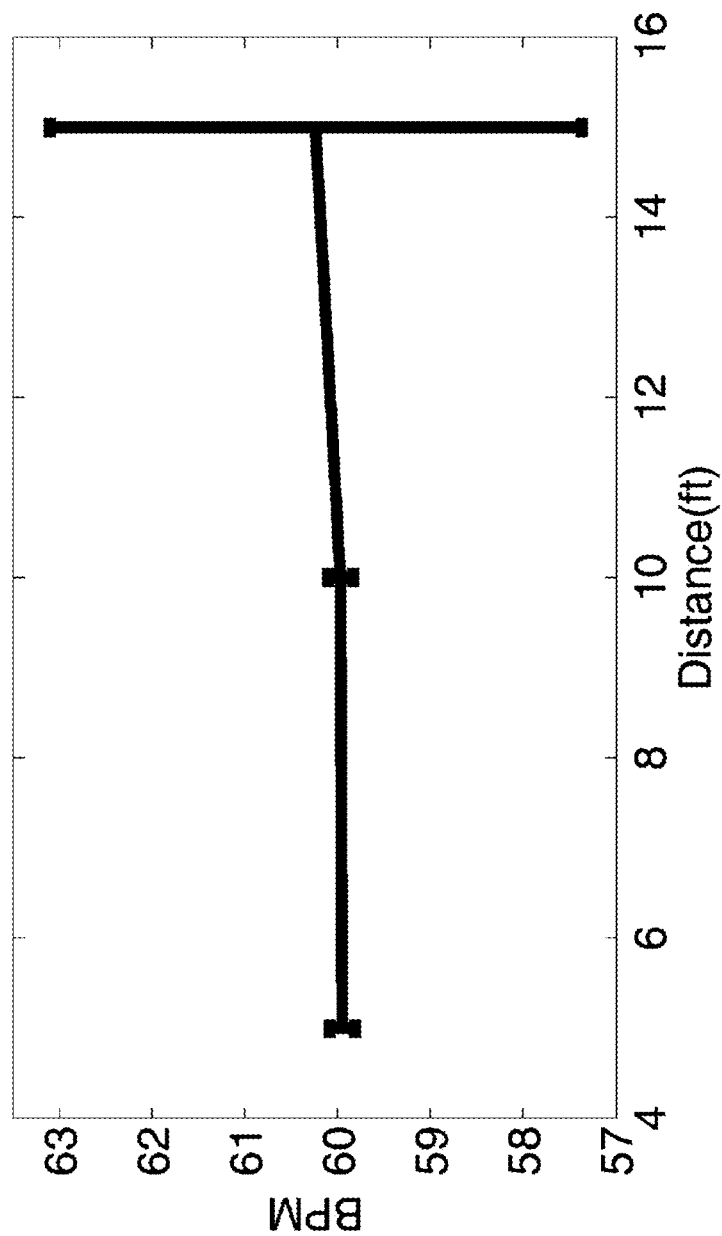
FIG. 5 is a graph of the mean and standard deviation observed in heart rate calculations over different tag-to-reader distances.

FIG. 5 pertains to the range of the system, i.e., the greatest distance between the RFID tag and the RFID reader that still results in acceptable system performance. The range of the system is dependent on two factors: the ability of the power harvester to obtain enough power to run the wearable component circuitry, and the ability of the reader to obtain data from the RFID tag sufficient to resolve the heart rate with acceptable accuracy.

To test the harvester range, the RFID reader component and the RFID tag component were separated by about five feet, a distance known to provide good system performance. The distance between them was gradually increased while monitoring the output of the heart rate detector on an oscilloscope. The harvester was observed to obtain enough power to continuously operate the RFID tag component circuitry up to a distance of about 11 feet from the reader. Beyond that distance, the harvester was observed to run the circuit only intermittently for a few seconds at a time. It is contemplated that this range may be improved by refining the circuitry of the power harvester.

To quantify the range limitations due to the reader's ability to resolve the heart rate, the distance between the RFID tag and the reader was set at a distance known to provide good resolution, and the standard deviation in measurement was calculated at different distances while increasing the distance between them. The standard deviation in the calculated heart rate was observed to remain within 1 BPM of the known actual heart rate up to about 10 feet, and deteriorated to about 3 BPM at 15 feet. The accuracy of the system can be improved at longer distances by increasing the sampling window, as described previously.

A second, non-system-related "dummy" RFID tag producing its own signal responsive to the RFID reader was added to the test environment to assess the system's performance in the presence of interference from proximate unrelated RFID tag. The dummy tag and the sensor tag were placed about one and a half feet from each other, and about three feet from the reader. It was expected that only about 50% of the reader measurements would be from the sensor tag, and the other 50% would be from the dummy tag. The following table shows the results for this arrangement at 60 BPM and 120 BPM. The table lists the average heart rate and standard deviation calculated over a four second sampling window, and also shows the percentage of false beats detected.

| HR (BPM) | Average HR (BPM) | Std. Dev. | False Beats |
|---|---|---|---|
| 60 | 60.37 | 0.92 | 0% |
| 120 | 120.1 | 2.4 | 0.5% |

It was observed that the performance suffered only slightly due to the presence of the dummy tag. It was determined that, as the reader spends time reading the dummy tag, the time between measurements of the sensor tag increases, thereby increasing the variation in the time between successive beats detected. It is also possible that the reader may not read the sensor tag for a duration longer than 100 ms, in which case the system would falsely detect a heartbeat. In spite of these errors, the system was found to calculate the heart rate fairly closely in this test.

The tests of the exemplary system in the test environment described in the foregoing confirms that the disclosed health information monitoring system, comprising an OOK modulated passive UHF RFID tag in conjunction with an RFID tag reader, can be used effectively to accurately determine the heart rate from an ECG signal. No information other than the tag identifier needs to be stored on the RFID tag. The system can be configured in large part using conventional RFID elements. The disclosed embodiments were found to consume less than 200 μW of peak power, suitable for battery-free operation using a wireless power harvester that obtains power from an RFID interrogation signal. Even though the beat to beat variability is typically low for normal heart rates, averaging over short time windows of just a few seconds has been demonstrated to product reliable results. An exemplary embodiment was tested and was observed to maintain acceptable performance up to a distance of about ten feet between the RFID tag and the RFID reader. The embodiment was also found to be effective even in the presence of a proximate unrelated RFID tag responding to the RFID interrogation signal.

However, in an actual operating environment there may be other sources of noise in an RFID based health data signal other than a single proximate extraneous RFID tag. Therefore, modified approaches to logistic regression were developed for accurate identification and determination of a health data signal from a passive RFID tag in a noisy environment. An RFID signal containing heart beat data was used as an exemplary health data signal, although the modified approaches may be applied to other passive RFID health data signals.

In one approach, a logistic regression model may first be used to determine which ones of a plurality of data points obtained in a noisy environment have a very high probability of pertaining to the heart beats being monitored. These data points are then used as features to remove ambiguity in the recognition of other heart beats from the same monitored source. This procedure is trained using parameters obtained from a single heart rate measurement, and the obtained parameters are used for determining various other heart rates. Using this approach, an $F_1$-score of 0.98 for correct heart beat detection was achieved, and an error of over 75% in mean heart rate calculation was completely eliminated.

Time-domain methods that essentially find average heart rates over several seconds can only help to overcome problems posed by poor data quality to a certain extent. Additionally, averaging removes beat-to-beat interval information which is required for heart rate variability analysis. Therefore, a method to identify individual heart beats more accurately from RFID data is required. Machine Learning algorithms have been employed for improving accuracy of other heart rate monitoring systems. However, a new logistic regression model is disclosed herein to improve heart beat detection from RFID data obtained using the wireless battery-free system disclosed in the foregoing description.

One exemplary approach is to accurately recognize heartbeats by identifying unintentional outages. RFID tag outages can be due to poor signal strength, interference due to other RFID tags or other noise sources. It is difficult to distinguish between a real heartbeat, indicated by an RFID tag turning off for a set time (e.g. 100 ms), and a false outage because the tag data is similar in both cases. Of course, if false or missing outages are perceived as heartbeats, the calculated heart rate will be incorrect. In addition, it may be advantageous to avoid the use of averaging over long measurement windows, because the beat-to-beat variability information is lost. A supervised learning algorithm based on logistic regression may achieve this goal. Logistic regression is a regression model in which the dependent variable (DV) is categorical. That is, the DV must be one of a limited, fixed, number of possible values. For example, a measurement by an RFID reader either indicates a valid heartbeat, or it doesn't. Thus, each measurement is assigned to an "on" group or an "off" group. In an exemplary approach probabilities are obtained from a logistic regression model to estimate the likelihood that a gap or outage in the RFID tag's backscatter signal indicates a genuine monitored heartbeat.

Figure 6:
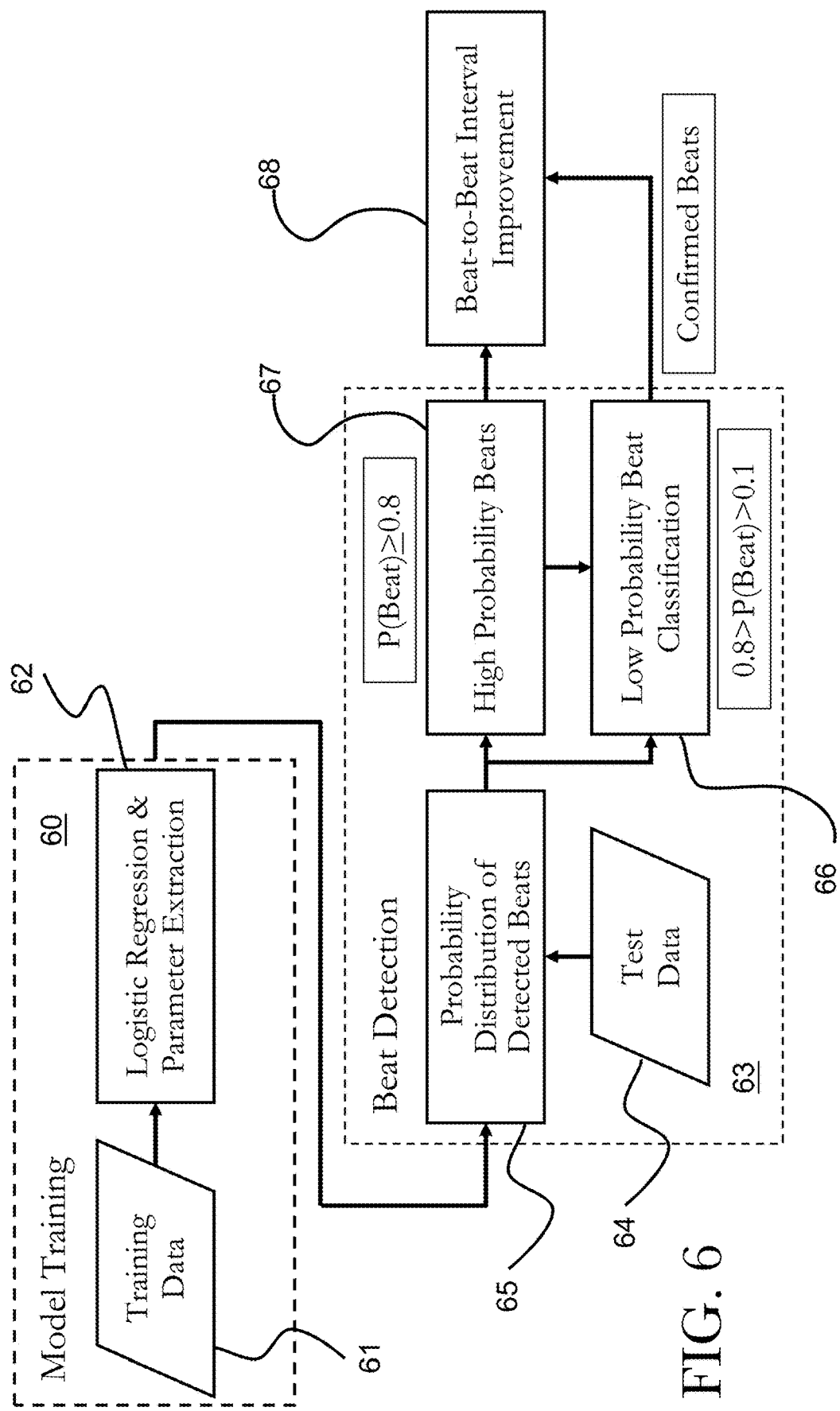
FIG. 6 is a flow diagram of an illustrative approach to probabilistic heart beat detection from data received by an RFID reader from an RFID tag responsive to an interrogation signal.

FIG. 6 is a flow diagram illustrating this approach. There are two main processes to perform. The first process is model training, indicated by dashed box 60. The goal for model training is to obtain parameters that fit already received data points as training data 61. The parameters can then be used in classifying subsequent data points correctly as beats or not-beats. The time between successive sensor RFID tag reads is used in the model. For data points that are not heartbeats, this time may be much shorter than the predetermined duration of the RFID outage. However, the time between tag reads for false outages could be much higher or comparable to the predetermined RFID outage duration. Hence, a linear fit cannot be used to separate the real beats from non-beats and false outages. Therefore, polynomial features of time between tag reads are used as input to the model. Each feature data point has an associated state; all real beats are assigned as "1" and all non-beats (including false outages) are assigned "0".

Figure 7:
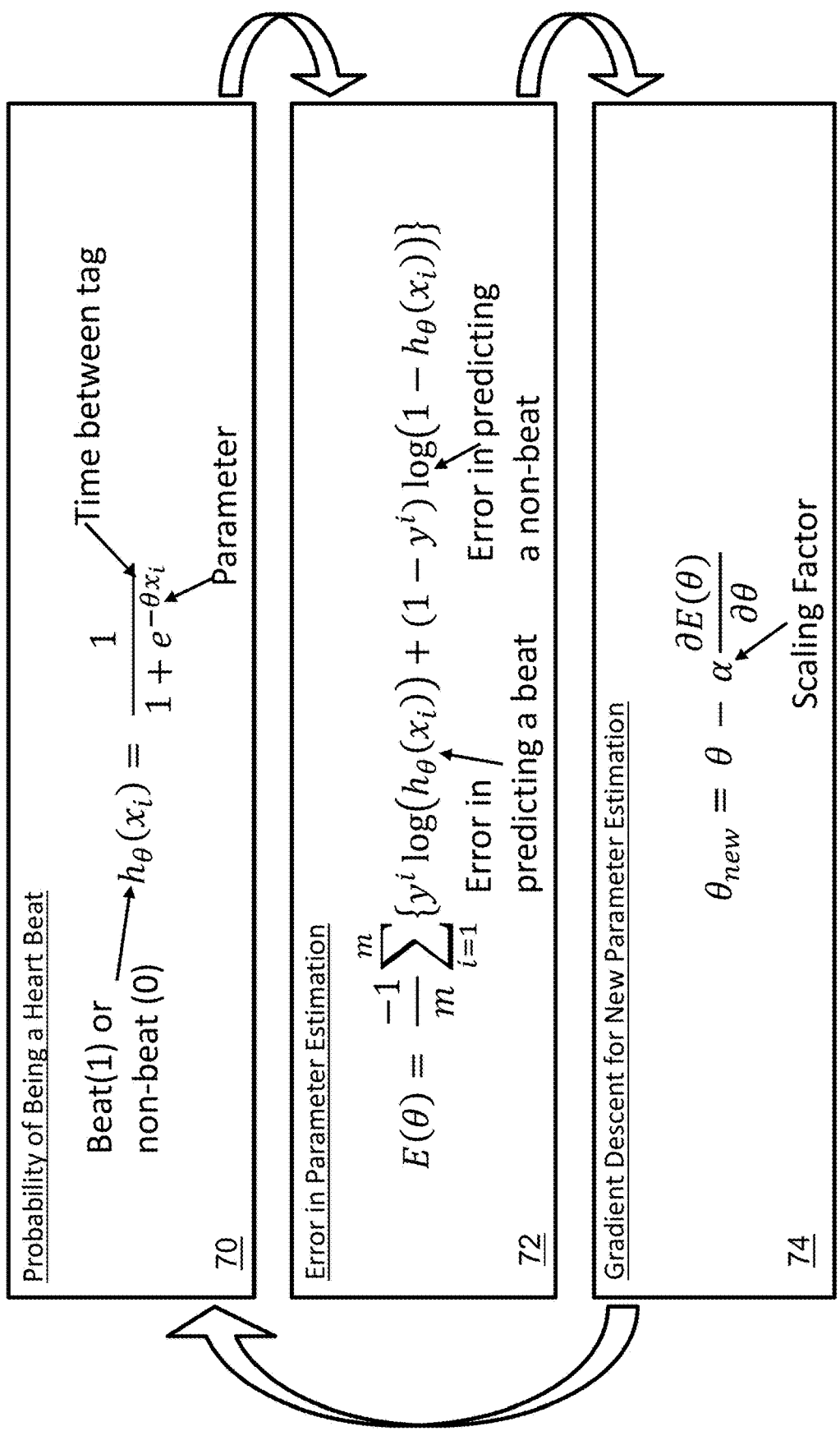
FIG. 7 is a flow chart showing a method of improving data recognition in a passive RFID-based signal in accordance with the disclosure.

Logistic regression and parameter extraction, 62, are illustrated in FIG. 7 and performed as follows. In block 70, the probability of a given tag reading being an actual heart beat is given by the logistic function in Eq. 2, $$h_\theta(x_i) = \frac{1}{1 + e^{-\theta x_i}} \quad (2)$$

where "$h_\theta(x_i)$" is the probability that a data point represents a beat (1) or not (0), "$x_i$" represents the training data feature with index "i", and "$\theta$" represents the parameters of the model. Before training, the parameters "$\theta$" for a fit are unknown. In block 72, the parameters are first assumed to be "0". The error with this assumption is calculated using Eq. 3, $$E(\theta) = \frac{-1}{m} \sum_{i=1}^{m} \{y^i \log(h_\theta(x_i)) + (1 - y^i)\log(1 - h_\theta(x_i))\} \quad (3)$$

where "m" is the number of training samples with index "i", and "y" is the actual state of the output (1 for beats and 0 otherwise). The first term in Eq. 3 accounts for the error in determining beats, and the second term represents the error in determining non-beats. In block 74, after the error due to the choice of θ is determined, a new estimate of θ may be calculated using Eq. 4, (4)

$$\theta_{new} = \theta - \alpha \frac{\partial E(\theta)}{\partial \theta} \quad (4)$$

where "α" is a scaling factor that adjusts the step sizes for new values of θ. The process returns to block 70, where the probability of a given tag reading being an actual heart beat is recalculated using the new θ values by the logistic function in Eq. 2, and the process continues iteratively from there. The process of finding the error and new parameters is continued until the value of θ converges, and that value is chosen as the parameter for the model.

Figure 8:
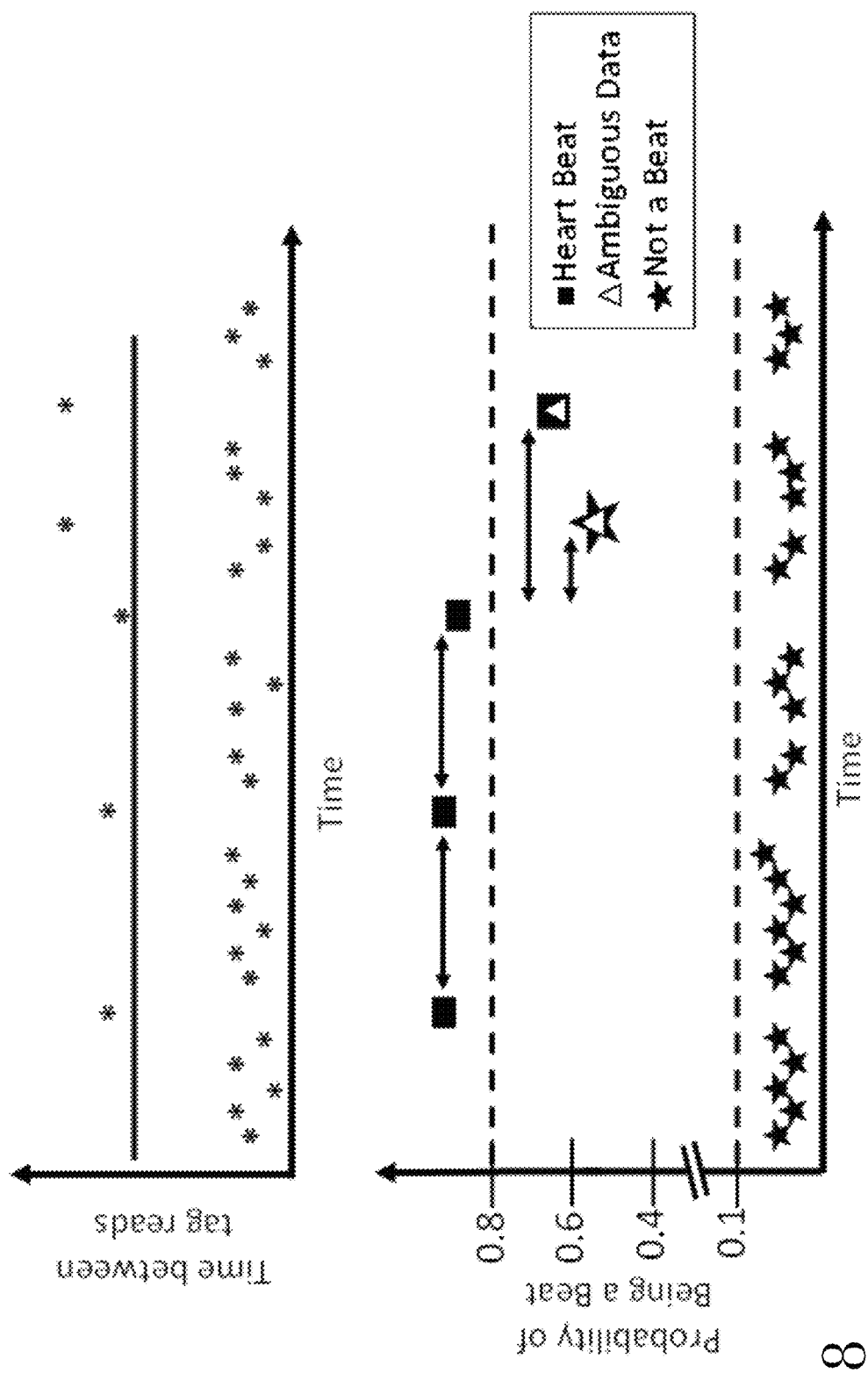
FIG. 8 illustrates the identification of heartbeats in a passive RFID-based signal.

The second process of the method is beat detection, indicated in FIG. 6 by dashed box 63. The parameters obtained from model training may be verified by inserting the test data features 64 into Eq. 2. The top graph in FIG. 8 plots the time periods between successive tag reads. The longer periods above line 80 occur as the RFID reader does not receive a signal because the RFID tag is off, then receives a signal again when the RFID tag comes back on. This operation yields the probability of each test data point being a heartbeat. The bottom graph of FIG. 8 shows how tag data are classified into three categories: heartbeats, non-beats, and ambiguous data, based on the probabilities obtained from the model. As shown in FIG. 8, tag data that have a probability of less than 0.1 of being an actual beat are classified as non-beats. Conversely, data points that have a greater than 0.8 probability of being a real beat are classified as beats. The two remaining data points in the bottom graph of FIG. 8 have intermediate probabilities, and they could represent real beats or false outages. To classify these ambiguous beats, a linear regression analysis is done using the previous two accurately determined beats. If an ambiguous data point follows the linear trend of the two known heartbeats within an appropriate margin, it may be classified as a heartbeat. An illustrative appropriate margin might be 20%.

Heartbeats can sometimes be missed due to a hardware glitch, noisy environment or incorrect classification from the above procedure. An example for a 60 BPM heart rate signal is shown in the following table in which the time between successive detected beats is shown in seconds.

| $T_{1-2}$ | $T_{2-3}$ | $T_{3-4}$ | $T_{4-5}$ | $T_{5-6}$ |
|---|---|---|---|---|
| 0.99 | 1.02 | 0.98 | 2.01 | 0.99 |

As shown in the table, the time between the fourth and fifth beat (T4-5) is twice as long as the previous three samples, which strongly indicates a missed beat. When such a case is encountered, a beat may be inserted using the arithmetic mean of the previous two beats.

Testing with actual data was performed to verify the procedure explained above. A commercial ECG simulator (HE Instruments' Tech-Patient Cardio ECG Simulator) was used as a source for the heart rate signal. The ECG simulator was used to generate three discrete heart rates; 45 BPM, 60 BPM and 120 BPM. The simulated ECG signal was fed into the RFID tag component of the heart rate monitoring system described herein. The test system controlled a passive RFID tag configured to transmit continuously by default, but to turn off for a period of 110 ms every time an ECG pulse was detected. Thus, a threshold of 110 ms between successive tag reads was expected to detect all transmitted heart beats. The RFID data was recorded by an Impinj Speedway Revolution R420 passive UHF tag reader. The RFID reader component and the RFID tag component of the tested system were placed six feet away from each other. A noisy signal environment was simulated by placing an additional RFID tag five centimeters away from the system's RFID tag. For each set of heart rate measurements, at least 7000 individual tag reads were processed and the time between successive responses from the sensor tag was calculated.

The 60 BPM heart rate data was used to train the model. The test had two goals; to identify heartbeats that the procedure under test warranted a high level of confidence, and to subject the ambiguous data points to further scrutiny. The true beats and the ambiguous data were cycled through the regression analysis described above. All but two of the actual beats were correctly identified, the first of which was the second beat of the data set and so did not have two previous beats for comparison. The missed beats were accounted for using the process described above. It should be noted that the entire process depends only upon past data and thus heart beat detection can be done in real-time.

Below, the $F_1$-score demonstrates the improvement, $$F1_{score} = \frac{2 \times \text{Precision} \times \text{Recall}}{\text{Precision} + \text{Recall}}$$

where "Precision" is the fraction of detected beats that are actual beats, and "Recall" is the fraction of actual beats that are detected. Thus an $F_1$ score of 1 indicates there are no false positives or false negatives. This procedure provides an improvement in detected heart beats over the threshold method for all heart rates tested. The $F_1$ score of the 120 BPM data without using the procedure is comparatively higher than others in the same column. The 120 BPM signal has twice as many heart beats as the 60 BPM signal in the same period, and the higher number of actual heart beats improves the fraction of actual beats detected, resulting in a higher $F_1$ score.

Figure 9:
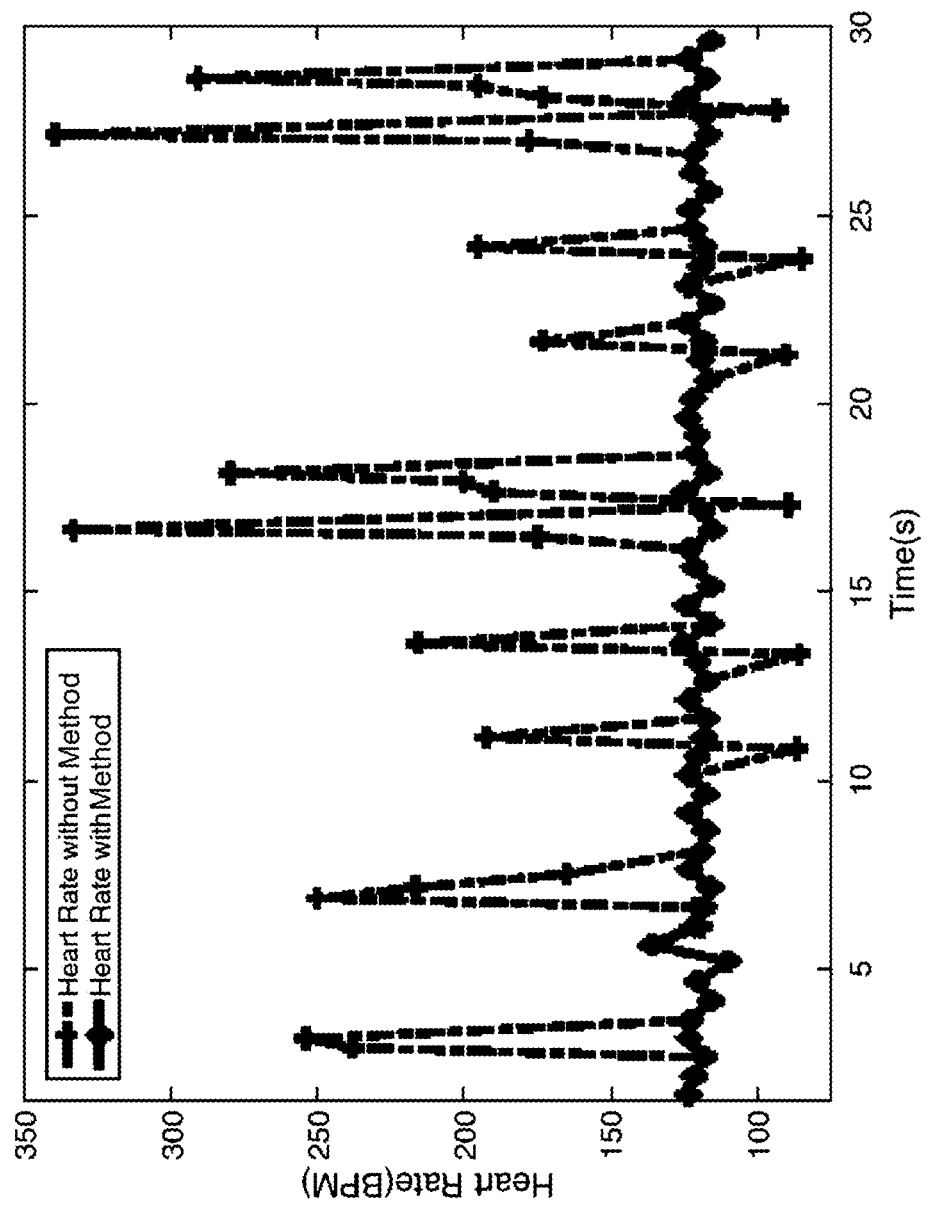
FIG. 9 is a graph of the calculated heart rate with and without using a method for improving heart rate calculation in accordance with the disclosure.

The calculated heart rate for a 120 BPM input signal with and without employing the method are compared in FIG. 9. Without the method, the heart rate is unstable and most of the error is due to false beats. These additional beats reduce time between detected beats causing a spike in the calculated heart rate. There are also sudden drops in calculated heart rate for the graph without the method. Here, the missed beats are not accounted for and this leads to a longer duration between detected heartbeats thereby causing a lower calculated heart rate.

As can be seen in FIG. 9, spikes are absent for heart rate with the method. The table below shows the calculated heart rate and corresponding error with and without using the method. As shown, without the method the calculated heart rate is overestimated by as much as 77%. This is mainly because of false outages which cause spurious spikes in calculated heart rate. The method successfully filters out these false outages to arrive at an accurate heart rate calculation.

| | Average Heart Rate (BPM) | | | |
|---|---|---|---|---|
| Heart Rate (BPM) | Without Method | Error | With Method | Error |
| 45 | 79.76 | 77.2% | 45.04 | 0.09% |
| 60 | 105.75 | 76.3% | 59.97 | 0.05% |
| 120 | 144.94 | 20.8% | 120.2 | 0.17% |

The disclosed logistic regression based model can be used to improve the detection of heart beats from RFID data. Parameters obtained by training the model using features from 60 BPM heart rate signal were used to improve the beat detection in 45 BPM and 120 BPM signals. The method works by first identifying data points that have a high probability of being real heart beats and uses them to accurately classify ambiguous heart beat data. A procedure is also employed to account for heart beats that are missed by the method to get a more robust overall heart rate calculation.

Although this method has been developed for RFID data, it may be possible to adapt it for other heart rate monitoring techniques that can use a threshold for detecting heartbeats, such as ballistocardiagraphy and pulseoximetry.

In another embodiment in which the RFID tag component may be used to monitor a subject's respiration, motion artifacts in the RFID tag component may be detected when it is worn by a subject, for example, as the subject's chest rises and falls with each breath. These motion artifacts may cause a change in the Returned Signal Strength Indication (RSSI) from the tag. RSSI values can be monitored to calculate the respiration rate.

In an exemplary embodiment for monitoring respiration rate, RSSI values may be collected over time, and a Kalman filter may be applied to the collected data to reduce noise artifacts in the wireless signal. Kalman filtering is a method that uses a series of measurements observed over time containing statistical noise and other inaccuracies, to produce estimates of unknown variables in the data. The filtered data are then grouped into discrete time windows, and statistical features are extracted from those windows to establish a baseline RSSI. For the respiratory application, it may not be possible to collect non-actuating test data since non-breathing test data is biologically infeasible. Therefore, single-class anomaly detection is required. Subsequent new windows of data are compared to the baseline to classify the window as corresponding to inhaling or exhaling. Using a programmable mannequin, a One-Class Support Vector Machine anomaly detector has been shown to perform with classification accuracy nearly as good as its two-class counterpart, and the FFT has been shown to accurately indicate movement of the passive RFID tag.

Conventional respiration monitoring devices may be uncomfortable to wear, and are subject to signal loss when the subject being monitored changes position or becomes mobile. In an embodiment of a wireless passive respiration monitoring system, devices may be knitted into the fabric of a wearable, wireless, smart garment. For example, conductive thread in the garment may act as an antenna inductively coupled to a Radio Frequency Identification (RFID) chip in the fabric. In this embodiment, the Received Signal Strength Indication (RSSI) may change as the knitted antenna is deformed due to stretching of the garment, to determine different types of motion in the inductively-coupled chip and knit antenna structure as it is moved by the wearer.

Figure 10:
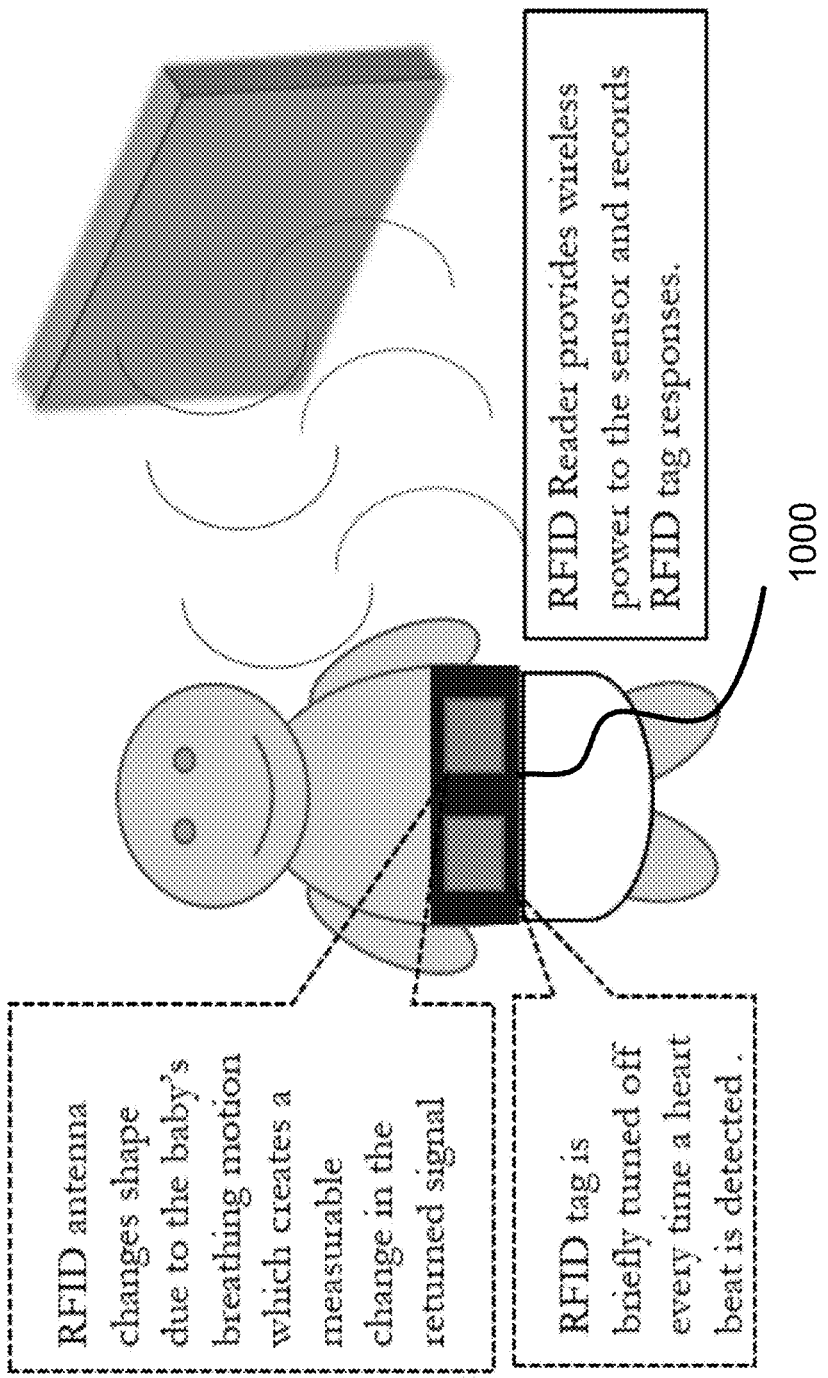
FIG. 10 illustrates a passive RFID monitoring system suitable for monitoring an infant's heart rate and respiration rate.
Figure 11:
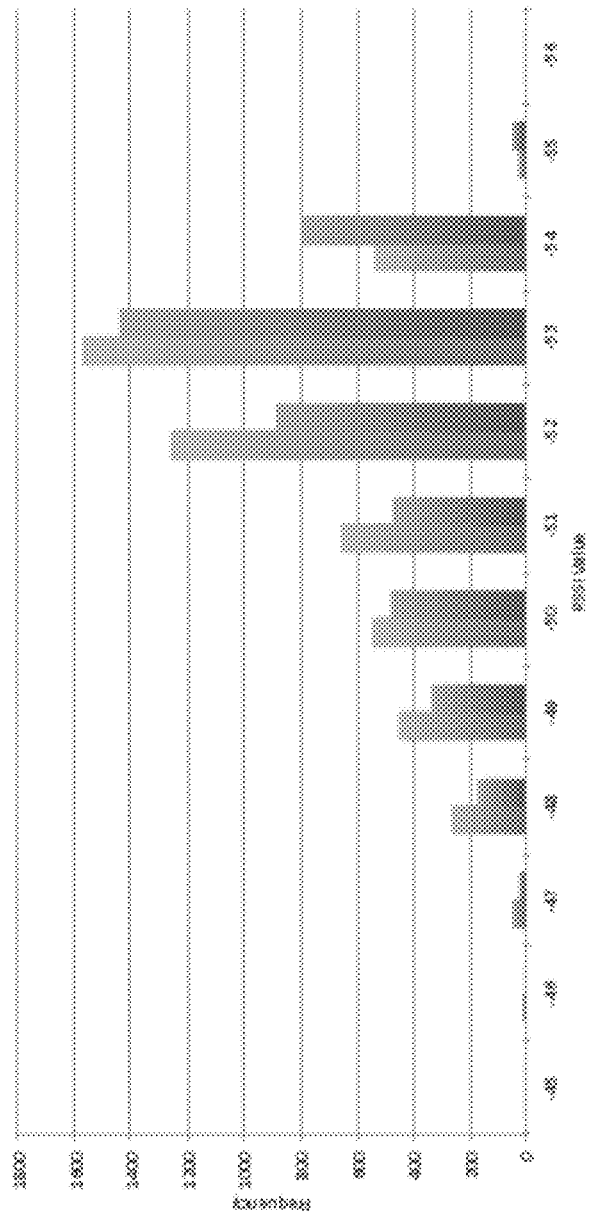
FIG. 11 is a bar graph illustrating respiration rate monitoring using passive RFID signaling.

Depending on the requirements of gathering health condition data, a plurality of RFID tags may be employed with different sensors, to provide power and to transmit data. For example, as shown in FIG. 10, an exemplary passive RFID tag based component 1000 may comprise a battery-free combination heart rate and respiration rate monitor having a separate RFID tag for each measurement. Machine learning algorithms may be used to accurately classify RFID data into heart beats and active respiration. A histogram of breathing (left bar of each pair) and heartbeat (right bar or each pair) RSSI values is shown in FIG. 11. Despite noticeable overlap, the breathing RSSI values tend to be larger than the heartbeat values. With filtering and signal-processing similar to that previously described, both the respiration rate and the heart rate of the subject may be determined from these RSSI values.

Figure 12:
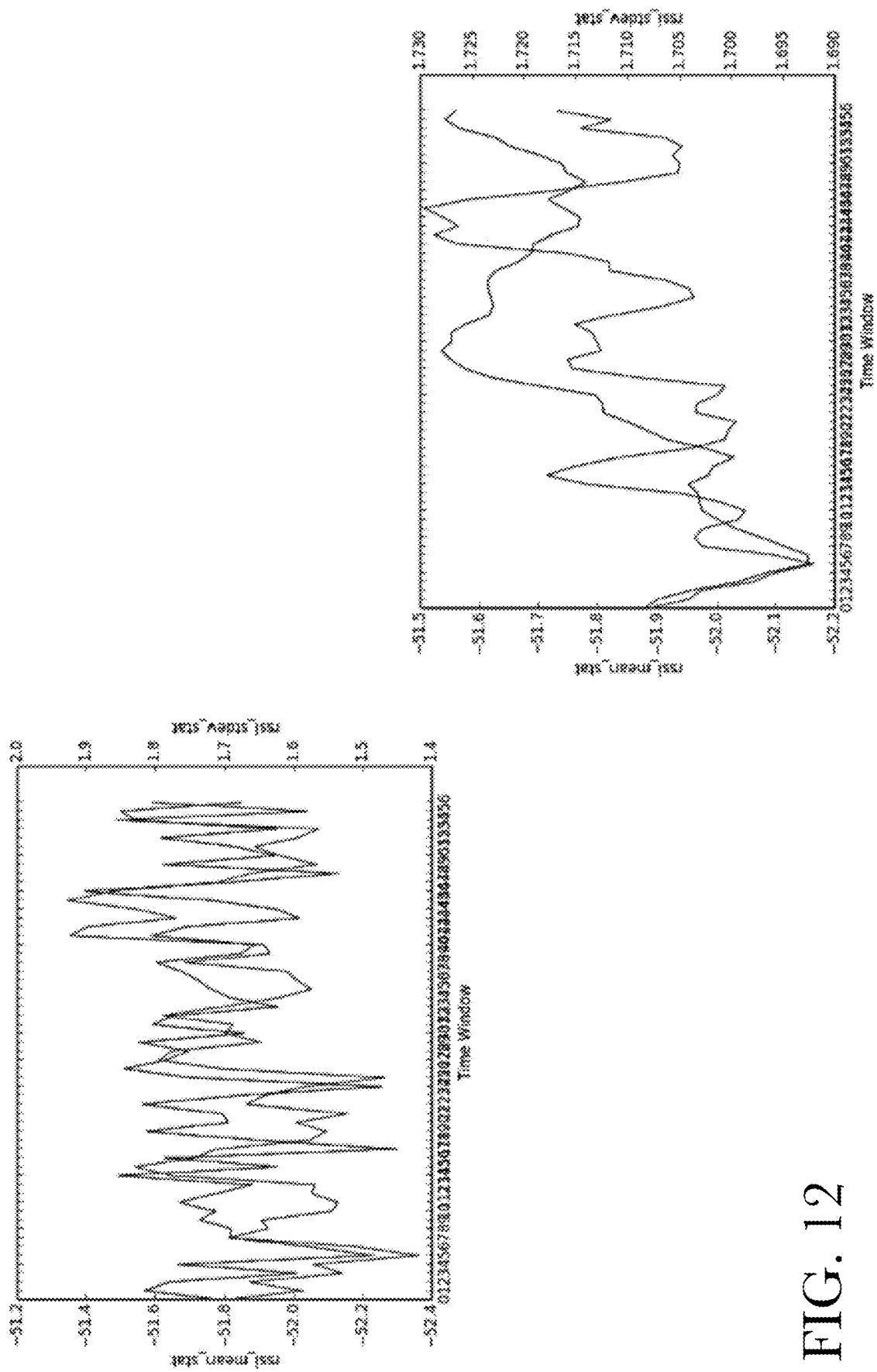
FIG. 12 illustrates the use of a Kalman filter in monitoring a subject's respiration rate using passive RFID signaling.

The only pre-processing required for heart rate determination may be the calculation of time between successive RFID tag responses. However, for respiration rate, it may be necessary to filter every N-seconds of data (the measurement window) using a Kalman filter due to the noisy output from the passive wireless RFID tag. No additional pre-processing of the data is needed, and this filtering can be done on each successive window rather than on the entire data set, facilitating real-time processing. FIG. 12 illustrates RFID respiratory data over time, with the average and standard deviation of each window plotted over 8-second time horizons. The data before Kalman filtering is shown at the top left of the figure, and after Kalman filtering is shown at the bottom right. The window values (x-axis) shown in red indicate exhaling, and blue indicate inhaling.

FIG. 13 illustrates an exemplary respiratory classification method that uses linear classifiers to classify inhaling and exhaling RFID data. A Support Vector Machine (SVM) separates the mean and standard deviation of windows of data into an inhaling class and an exhaling class. The SVM requires training data for both classes, which is biologically infeasible for the exhaling class (as this would require the subject not to inhale). This can be overcome by using a single-class SVM classifier, which assumes that any data point outside an "envelope" of observed training data is an anomaly. However, these anomalies are observed to occur only in specific regions relative to the training envelope.

By filtering and utilizing a Support Vector Machine for classification, it is possible to classify up to about 94% of respiratory data points accurately (calculated by so-called Receiver Operating Characteristic-Area Under the Curve "ROC-AUC"), using a window size of approximately 4 seconds (128 data points per window collected at 30 Hz), and a training set size of approximately 2.5 minutes.

It is contemplated that practical wearable passive RFID tag based devices can be manufactured having a small form factor, for example by integrating some or all of the components illustrated in the reference numeral 26 dashed box in FIG. 2 with signaling antennas on a single flexible circuit board no larger than a standard credit card. Such devices may be incorporated into garments or may be provided with a wearable strap or harness. Advantageously, the user never has to replace or recharge a battery or perform any other maintenance. Such a device may be used for example as a mobile heart rate monitor for patients in healthcare facilities, as a comfortable cardiac/respiration monitor for infants in cribs, and the like. The disclosed wireless monitor system may also be used during exercise, for example on aerobic exercise machines such as treadmills, stationary bikes, and the like.

Although embodiments and aspects of the invention have been disclosed with a certain degree of particularity, the description and figures have been made by way of example only. A person of ordinary skill in the art would understand that numerous changes in the details of construction, combination, and arrangement of parts and steps may be made without departing from the scope of the disclosure. Accordingly, such changes are deemed to be included within the scope of the invention, the protected scope of which is defined by the claims. Accordingly, the invention is not limited except as by the appended claims and the elements explicitly recited therein.

The invention claimed is:

1. A passive RFID health monitoring device, comprising:
an antenna for receiving a continuous interrogation signal;
a passive RFID chip coupled to the antenna comprising:
    a power harvester circuit coupled to the antenna that obtains power from the interrogation signal and converts it to direct current (DC) to provide operating power for at least one other circuit in the passive RFID chip;
    a health data amplifier circuit coupled to the power harvester circuit and having at least one port for receiving a cyclical health data signal from at least one sensor, the health data amplifier circuit operative to receive operating power from the power harvester circuit and use the power to amplify the received cyclical health data signal;
    a data detector circuit coupled to the health data amplifier circuit that receives the amplified cyclical health data signal and detects the occurrence of at least one event of interest in each cycle of the cyclical health data signal, and outputs a signal containing information of each detected event of interest; and
    a passive RFID tag coupled to an antenna and operative to output via the antenna a default continuous backscatter signal responsive to the received interrogation signal, the RFID tag coupled to the data detector circuit to receive the signal containing information of each detected event of interest, and further operative to modify the backscatter signal to include at least a portion of the information of each detected event of interest;
wherein the cyclical health data signal includes at least one electrocardiographic (ECG) signal from at least one ECG sensor operationally coupled to a subject, the ECG signal containing information of the condition of the subject's heart;

wherein the event of interest is the occurrence of the peak of a QRS Complex (R) in each cycle of the ECG signal;
wherein the data detector is a heart rate detector that detects the peak of the R event in each cycle, the heart rate detector configured to output a pulsed binary waveform that switches from a first value to a second value when it detects the peak of the R event, remains at the second value for a predetermined duration, and returns to the first state at the end of the predetermined duration.

2. The device of claim 1, wherein the RFID tag does not output the continuous backscatter signal when the pulsed binary waveform has the second value, and does output the backscatter signal when the pulsed binary waveform has the first value.

3. The device of claim 1, wherein the cyclical health data signal includes a respiration signal that arises in at least one respiration sensor responsive to a cyclical motion caused by a subject's breathing, wherein:
the health data amplifier circuit has at least one port for receiving the respiration signal from the at least one respiration sensor and amplifies the respiration signal;
the data detector circuit is a respiration detector that receives the amplified respiration signal and detects the occurrence of at least one event of interest in each cycle of the respiration signal, and outputs a waveform containing information of the subject's respiration corresponding to the detected event of interest; and
the passive RFID tag is coupled to the respiration detector to receive the waveform containing the information of the subject's respiration, and is operative to modify the backscatter signal to include at least a portion of the information of the subject's respiration.

4. A passive RFID health monitor system, comprising:
the passive RFID health monitoring device of claim 1;
an RFID reader inductively coupled to the passive RFID health monitoring device, and containing a data processor operative to obtain and perform operations on the health information included in the modified backscatter signal from the RFID tag of the RFID health monitoring device.

5. The system of claim 4, wherein the operations performed on the obtained health information include calculating a rate of occurrences per minute of the cyclical health data signal sensed by the at least one sensor.

6. The system of claim 5, wherein the rate is one of a heart rate and a respiration rate.

7. A passive RFID health monitoring device, comprising:
an antenna for receiving a continuous interrogation signal;
a passive RFID chip coupled to the antenna comprising:
a power harvester circuit coupled to the antenna that obtains power from the interrogation signal and converts it to direct current (DC) to provide operating power for at least one other circuit in the passive RFID chip;
a health data amplifier circuit coupled to the power harvester circuit and having at least one port for receiving a cyclical health data signal from at least one sensor, the health data amplifier circuit operative to receive operating power from the power harvester circuit and use the power to amplify the received cyclical health data signal;
a data detector circuit coupled to the health data amplifier circuit that receives the amplified cyclical health data signal and detects the occurrence of at least one event of interest in each cycle of the cyclical health data signal, and outputs a signal containing information of each detected event of interest; and
a passive RFID tag coupled to an antenna and operative to output via the antenna a default continuous backscatter signal responsive to the received interrogation signal, the RFID tag coupled to the data detector circuit to receive the signal containing information of each detected event of interest, and further operative to modify the backscatter signal to include at least a portion of the information of each detected event of interest;
wherein the RFID tag uses on-off keying (OOK) to transmit heart rate such that the RFID tag is turned on by default, and turned off when the signal containing information of each detected event of interest is detected;
wherein the cyclical health data signal includes at least one electrocardiographic (ECG) signal from at least one ECG sensor operationally coupled to a subject, the ECG signal containing information of the condition of the subject's heart; wherein the event of interest is the occurrence of the peak of a QRS Complex (R) in each cycle of the ECG signal;
wherein the data detector is a heart rate detector that detects the peak of the R event in each cycle, the heart rate detector configured to output a pulsed binary waveform that switches from a first value to a second value when it detects the peak of the R event, remains at the second value for a predetermined duration, and returns to the first state at the end of the predetermined duration.

* * * * *